(12) United States Patent
Ju et al.

(10) Patent No.: US 6,572,815 B1
(45) Date of Patent: Jun. 3, 2003

(54) TITANIUM HAVING IMPROVED CASTABILITY

(75) Inventors: Chien-Ping Ju, Room 607, No. 350, Tung Feng Rd., Tainan (TW); Jiin-Huey Chern Lin, No. 18, Lane 725, Chiu Ju 4 Rd., Ku Shan District, Kaohsiung (TW); Wen-Wei Cheng, Miaoli (TW)

(73) Assignees: Chien-Ping Ju, Tainan (TW); Jiin-Huey Chern Lin, Kaohsiung (TW)

( * ) Notice: Subject to any disclaimer, the term of this patent is extended or adjusted under 35 U.S.C. 154(b) by 0 days.

(21) Appl. No.: 09/548,266

(22) Filed: Apr. 12, 2000

(51) Int. Cl.$^7$ .............................................. C22C 14/00
(52) U.S. Cl. ........................ 420/421; 148/421; 148/538
(58) Field of Search ................................ 420/417, 421; 148/421, 538

(56) References Cited

U.S. PATENT DOCUMENTS

| | | | | |
|---|---|---|---|---|
| 2,766,113 A | * | 10/1956 | Chisholm et al. | 75/84.5 |
| 2,797,996 A | * | 7/1957 | Jafee et al. | 75/175.5 |
| RE27,286 E | * | 2/1972 | Bertea et al. | 75/175.5 |
| 4,253,933 A | * | 3/1981 | Sato et al. | 204/293 |
| 4,634,478 A | * | 1/1987 | Shimogori et al. | 148/421 |
| 4,810,465 A | * | 3/1989 | Kimura et al. | 420/417 |

* cited by examiner

*Primary Examiner*—John Sheehan
*Assistant Examiner*—Andrew L. Oltmans
(74) *Attorney, Agent, or Firm*—Bacon & Thomas

(57) ABSTRACT

The present invention provides a low alloying element-doped titanium and a casting cast therefrom. The doped titanium of the present invention includes titanium and from about 0.01 to 3 percent by weight of an alloying metal selected from the group consisting of bismuth, silver, hafnium, tantalum, molybdenum, tin, niobium, chromium and copper based on the weight of the titanium. The doped titanium of the present invention has improved castability and a decreased surface tension compared with pure titanium.

3 Claims, 12 Drawing Sheets

(2 of 12 Drawing Sheet(s) Filed in Color)

TITANIUM HAVING IMPROVED CASTABILITY

BACKGROUND OF THE INVENTION

1. Field of the Invention

The present invention relates to a titanium, and more particularly to a titanium casting. The titanium possesses improved castability and is suitable for use in biomedical implants and other applications.

2. Description of the Prior Art

Due to its lightweight, high strength-to-weight ratio, low elastic modulus, superior chemical corrosion resistance, and excellent mechanical properties at high temperature up to 550° C., titanium and its alloys have been widely used on aerospace, chemical, sports, and marine industries. Their superior biocompatability also makes them ideal as the primary materials used in dental and osteological restorations or implants, such as artificial bone pins, bone plates, shoulders, elbows, hips, knees and other joints, and dental orthopraxy lines.

A number of methods for fabricating titanium and its alloys with a desired shape have been developed. Among these, precision casting is the most difficult. Precision casting has the advantage that the cast produced has a near net shape, which greatly decreases the titanium fabrication cost. Also, precision casting is particularly suitable for producing objects with a small volume, high size accuracy, and complicated shape, for example in dental and osteological fields. However, if the difficulty in precision casting could be solved and the cost reduced, titanium and its alloys could even be utilized in many other everyday products.

There are many factors that affect the process of the precision casting and the properties of castings. According to the research results issued by Luk et al., in Dent. Mater., 8, 89–99,1992, the factors includes alloy composition, alloy density, alloy surface tension, casting temperature, investment material type, mold temperature, casting machine type, casting surface area/volume ratio, and pouring angle. The castability test is the most frequently used method for assessing various titanium precision casting processes. Castability is the ability of a molten alloy to completely fill a mold space. Castability is a combination factor, and there is no international standard for assessing it today. Since castability is affected by many factors, researchers have designed various test methods in accordance with various cast patterns for assessing the castability. The cast patterns includes spiral wax molds, fibrous nylon lines produced by injection molding (Howard et al., JDR, 59, 824–830, 1980), saucer-like molds, cylindrical molds, rectangle sheets, nylon mesh, and taper molds (Mueller et al., J. of Prosth. Den., 69, 367, Abstr. 2072, 1993). A wax mold of a simulated crown has also been designed (Bessing et al., Acta Odontology Scandinavian, 44, 165–172, 1986).

Titanium is inherently difficult to cast due to its high melting point and high reactivity. Its low density is another problem in casting. Therefore, the improvement of casting process is the main issue of titanium precision casting. The casting machines used at present utilize argon as the protective atmosphere to prevent high temperature reactions. Induction or arc is used as the heat source in order to shorten melting time as well as lessen high temperature reactivity. At present, in order to increase the pouring force and to avoid casting defect caused by poor flowability of the molten metal, the titanium casting machines can be roughly divided into the centrifugal casting type, the vacuum-pressure type, and the centrifugal-vacuum pressure mixed type (Yoshiaki, Conference Paper, 1–7, Australia, 1995).

A number of patents improving the castability of metal and metal alloy by means of different casting methods and machines have been issued. U.S. Pat. No. 4,763,717 issued to Lajoye et al. discloses a method utilizing a compact assembly for melting and centrifugal casting of metals. The melting is accomplished entirely in a vacuum condition, thereby avoiding the formation of oxides or other compounds. U.S. Pat. No. 5,065,809 issued to Sato et al. discloses a method for casting titanium or a titanium-based alloy by fusing the metal in a vacuum furnace while introducing argon gas therein and casting the resultant melts in mold. U.S. Pat. No. 5,119,865 issued to Mae et al. discloses a method for centrifugal casting titanium or a titanium-based alloy by using a Cu-alloy mold. The mold body is made of a copper alloy satisfying the following relationship: Ts+0.3.rho..gtoreq.70 where Ts is the tensile strength (kg/mm$^2$), and .rho. is the electrical conductance (% IACS). A cavity disposed in the mold body has a volume that is at most 30% of the volume of the mold body. U.S. Pat. Nos. 5,168,917 and 5,168,918 issued to Okuda et al. disclose a method for casting dental metals, which is characterized by positioning a dental metal ingot on the crucible, evacuating the casting chamber to vacuum, feeding a small amount of an inert gas at such a pressure as to induce arc discharge all over the upper surface of the ingot, thereby melting the ingot placed on the crucible by arc discharge from the arc electrode, pouring the thus obtained molten metal into a mold through its inlet, and immediately feeding an additional amount of the inert gas into the casting chamber to increase its internal pressure to a level suitable for casting. U.S. Pat. No. 5,193,607 issued to Demukai et al. discloses a method for precision casting titanium or titanium. The method includes establishing molten metal by induction heating in an assembly formed with water cooled copper segments disposed radially on the inside of an induction coil in a state insulated form each other and casting the molten metal into a permeable mold by vacuum casting. U.S. Pat. Nos. 5,267,602 and 5,392,842 issued to Volpe disclose a method for casting metal by melting it in a crucible over a hole too small to enable gravity to make the molten metal pass through the hole, after which increased pressure is applied to the metal to drive it through the hole into a mold. U.S. Pat. No. 5,626,179 issued to Choudhury et al. discloses a method for centrifugal casting titanium or a titanium-based alloy by using a reusable mold. The mold, at least in the area of the surface which comes in contact with the melt, consists of at least one metal selected from the group consisting of tantalum, niobium, zirconium, and/or their alloys.

Research has been conducted for improving the castability of metal and metal alloy by means of mixing various alloys. Asgar and Kaminski indicate that the alloy compositions of base metal alloys, high fusion noble metal alloys, or conventional type III gold alloys have a certain effect upon castability (Asgar et al., J. of Prosth.Dentistry, Vol. 54, No.1, 60–63, 1985; Kaminski et al., J. of Prosth Dentistry, Vol. 53, No.3, 329–332, 1985). Vincent et al. investigated the castability of five alloys, Thermocraft (atthey Garrett Pty. Ltd., Brisbane, Queensland, Australia), Degudent Universal (Degussa, Pforzheim, Germany), Victory (Unitek Corporation, Monrovia, Calif.), Ul-tratek (metals for Modern Dentistry, Inc., Danville, Calif.), and Wiron S (Bego, Bremen, Germany). The results indicated that castability is related to density and problems caused by low density may be solved by adjusting equipment, investment, and casting techniques to increase casting force (Vincent et al., J. of Prosth. Dent., 37, 527–536, 1977). Cohen et al. had studied the influence of beryllium on castability of Ni-Cr alloys and indicated that Be content exceeding 1% may be desirable in order to obtain optimal castability (Cohen et al., JDR, Abstr.609, 1991). Bessing et al. evaluated the castability of the simulated crowns of two low-gold alloys and two kinds of Ag-Pd alloys. It is found that the castability of the two low-gold alloys is comparable with that of the conventional type III gold alloys (Bessing et al., Swed. Dent. J., 16, 109–113, 1992). Most of the above-mentioned research was related to noble metals or its alloys and base metal alloys (such as nickel-chromium alloys). The casting of titanium and titanium is seldom mentioned.

The following are some related U.S. Patents about the alloying metals added to titanium or titanium. U.S. Pat. No. 4,830,823 issued to Nakamura discloses that it is preferable to cast a titanium containing aluminum at a ratio of 1.5 to 4.0% by weight and vanadium at a ratio of 1.0 to 3.0% by weight. In particular, the castings obtained by casting a "Ti-3Al-2.5V alloy" containing aluminum at a ratio 3.0% by weight and vanadium at a ratio of 2.5% by weight exhibit physical characteristics equal to those incidental to the Ti-6Al-4V alloy and superior to that of pure titanium castings. In the case where the Ti-6Al-4V alloy itself is cast, superior characteristics incidental to said alloy are lost and as a result, it becomes hard and brittle, whereby it cannot be used as cast. U.S. Pat. No. 5,091,148 issued to Prasad discloses that the addition of 0.01 to 0.5 wt % of one or more alloying metals of ruthenium, rhodium, hafnium or strontium into a titanium-aluminum alloy (such as Ti5Al2Sn, Ti6Al7Nb, or Ti6Al4V) can increase the corrosion and tarnish resistance. However, aluminum and vanadium have adverse effect in human health and are controversial for use as biomedical implants.

SUMMARY OF THE INVENTION

The object of the present invention is to solve the above-mentioned problems and to provide a titanium having improved castabiliby and a decreased surface tension compared with pure titanium.

To achieve this object, the titanium of the present invention includes titanium and from about 0.01 to 3 percent by weight of an alloying metal selected from the group consisting of bismuth, silver, hafnium, tantalum, molybdenum, tin, niobium, chromium and copper based on the weight of the titanium.

The present invention also provides a casting cast from the titanium mentioned above.

BRIEF DESCRIPION OF THE DRAWINGS

This application contains at least one drawing executed in color.

The present invention will be described in detail with reference to the illustrated embodiments and the accompany drawings, in which.

DETAILED DESCRIPTION OF THE INVENTION

Figure 1:
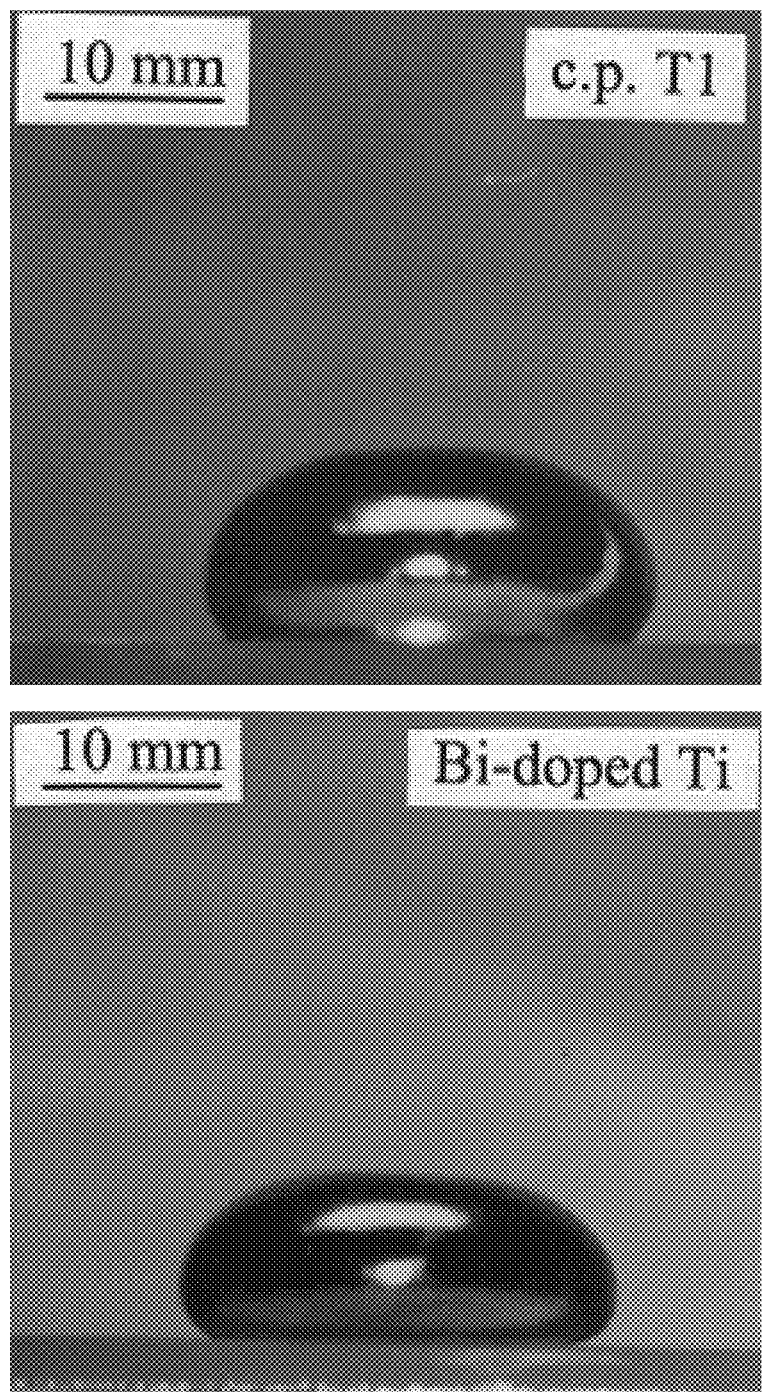
FIG. 1 shows the photographs of ingots of (a) pure titanium and (b) the titanium containing 1 wt % of Bi.

According to the present invention, the castability of titanium is improved by adding an alloying metal. The alloying metal can be bismuth, silver, hafnium, tantalum, molybdenum, tin, niobium, chromium and copper. The amount of the alloying metal is between 0.01 to 3 percent by weight based on the weight of the titanium.

In order to evaluate the castability of the titanium of the present invention, conventional methods of melting and casting titanium or titanium may be used. For example, argon arc fusion, high-frequency fusion and the like are suitable methods of melting alloys to be cast. In addition, a conventional casting method, such as centrifugal casting, suction-pressure casting, and vacuum-pressure casting can be adopted. The melting and casting conditions are not specially limited. The casting may be carried out at a temperature of the mold material of normal temperature to about 400° C.

The titanium of the present invention can be melted in a conventional hearth or crucible, which can be made of a ceramic such as magnesium oxide, calcium oxide, or zirconium oxide, or a metal such as copper. Preferably, the titanium of the present invention is melted in a copper crucible and the heat source is high energy electric arc. Thus, the melting time can be shortened, and reactivity of titanium at high temperatures can be reduced. In addition, copper has a very weak reactivity with titanium, which is beneficial.

X-ray diffraction (XRD) for phase analysis was conducted using a Rigaku diffractometer (Rigaku D-max IIIV, Rigaku Co., Tokyo, Japan) operated at 30 kV and 20 mA. A Ni-filtered CuK α radiation was used for this study. Phases were identified by matching each characteristic peak with JCPDS files. Microstructural examination of the series of cast metals was performed using an optical microscope (Leica TMX 100, Germany). Surfaces of these materials for light microscopy were mechanically polished via a standard metallographic procedure to a final level of 0.05 $\mu$m alumina powder, followed by chemical etching in a solution of water, nitric acid, and hydrofluoric acid (85:10:5 in volume).

The microhardness of the various castings was measured using a Matsuzawa MXT70 microhardness tester at a load of 200 gm for a duration of 15 seconds. To evaluate mechanical properties of the series of titanium systems, three-point bending tests were performed using a desk-top mechanical tester (Shimadzu AGS-500D, Tokyo, Japan) . The bending strengths were determined from the equation, $\sigma = 3PL/2bh^2$, where $\sigma$ is bending strength (MPa); P is load (kg); L is span length (mm); and b is specimen thickness (mm). The dimensions of the specimens for testing were: L=30 mm, b=5.0 mm and h=1.0 mm. The modulus of elasticity in bending is calculated from the load increment and the corresponding deflection increment between the two points on the straight line as far apart as possible using the equation, $E=L^3\Delta p/4bh^3\Delta\delta$, where E is modulus of elasticity in bending (Pa); $\Delta p$ is load increment as measured from preload (N); and $\Delta\delta$ is deflection increment at mid-span as measured from preload. The average bending strengths and moduli of elasticity were taken from at least five tests under each condition. The bending tests were performed on cast c.p. Ti as well as the same seven doped titanium systems cast in graphite mold.

EXAMPLE

In the following, 1% by weight of a metal of bismuth, silver, hafnium, tantalum, molybdenum, tin, niobium, chromium or copper was added as the alloying metal into titanium, melted, and then cast. Castability of the titanium systems were then measured.

The raw titanium used in the example was grade II commercially pure titanium. The pure titanium was mechanically ground to remove the oxide layer on the surface and then ultrasonically cleaned in acetone for 30 minutes to wash the oil on the surface. The alloying metal used in the example had purity higher than 99.5%.

The melting and casting were conducted using an arc-melting vacuum-pressure type casting machine. The pure titanium and 1 wt % alloying metal doped titanium were melt in a U-shaped copper crucible in a melting chamber. The whole melting process was conducted in an argon atmosphere and the heat source was high energy electric arc. The pressure of argon was 1.8 kgf/cm$^2$, and the melting time was 18 seconds. After solidification/cooling in the same chamber in argon atmosphere, the more or less oxidized/contaminated surface layer of the ingot was removed by mechanical grinding and the surface was ultrasonically cleaned in acetone. Each ingot was re-melted three times to improve chemical homogeneity. FIG. 1 shows the ingots of (a) pure titanium and (b) titanium containing 1 wt % of Bi. It can be seen that the Bi-containing titanium ingot is flatter than the pure titanium ingot, indicating that the addition of bismuth greatly decreases the surface tension of titanium, which is beneficial to the castability.

Castability was evaluated by means of casting the titanium in a mold made of copper or graphite.

Figure 2:
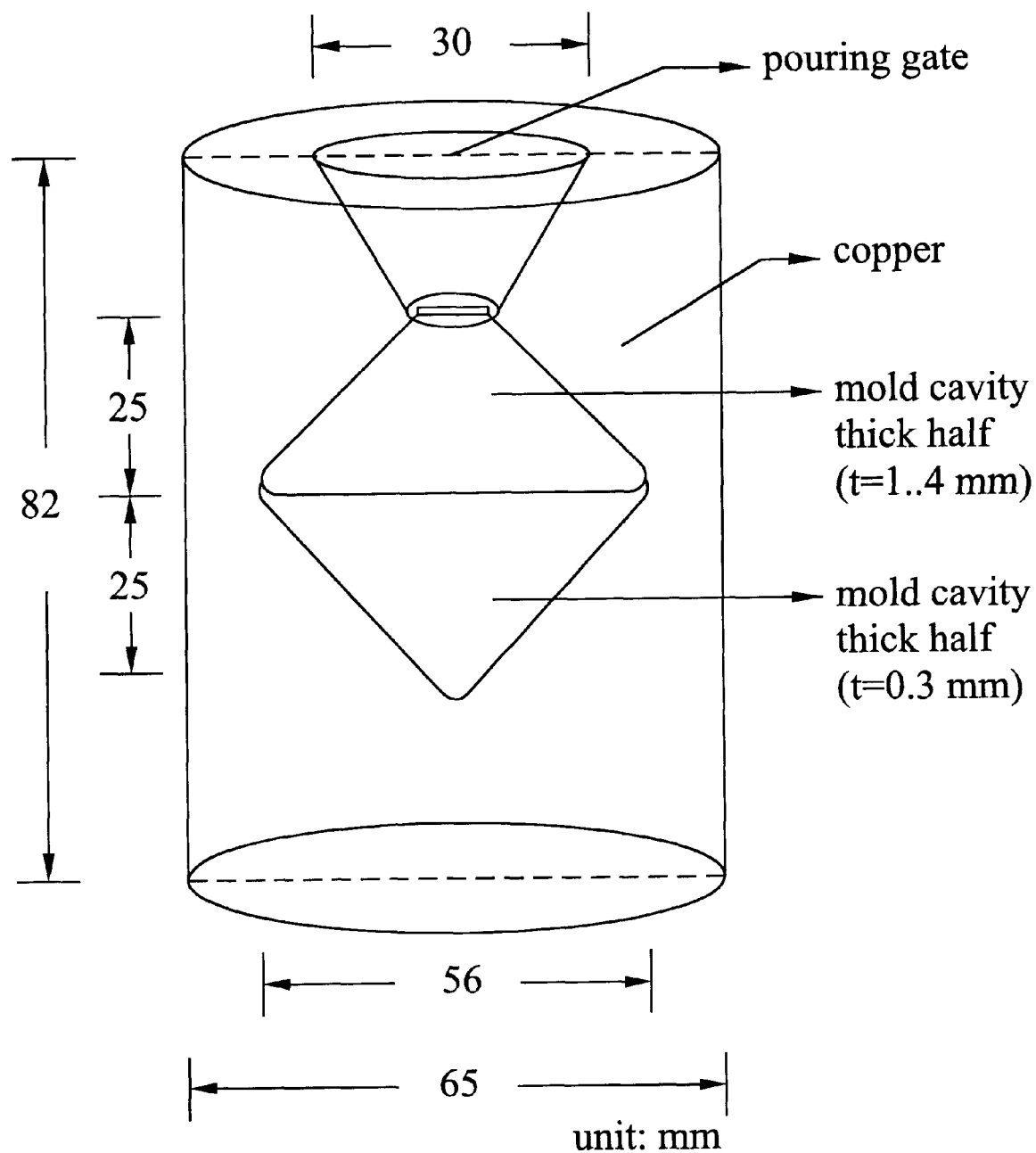
FIG. 2 is a schematic drawing showing the copper mold used for the castability test in this invention.

The copper mold used in the present invention is shown in FIG. 2 and was similar to the wax pattern used in Takahashi (M. Takahashi, "Casting of Titanium: Mold Materials", The third International Symposium on Titanium in Dentistry, Leura, New South Wales, Australia, August 29–31, p31–38, 1995). The copper mold cavity was composed of a thicker (1.4 mm) top half and a thinner (0.3 mm) bottom half, which was designed for simulating the full denture plates. The casting conditions were as follows: the argon pressure was 1.8 kgf/cm$^2$, the casting time was 18 seconds, and the casting temperature was room temperature.

Figure 3:
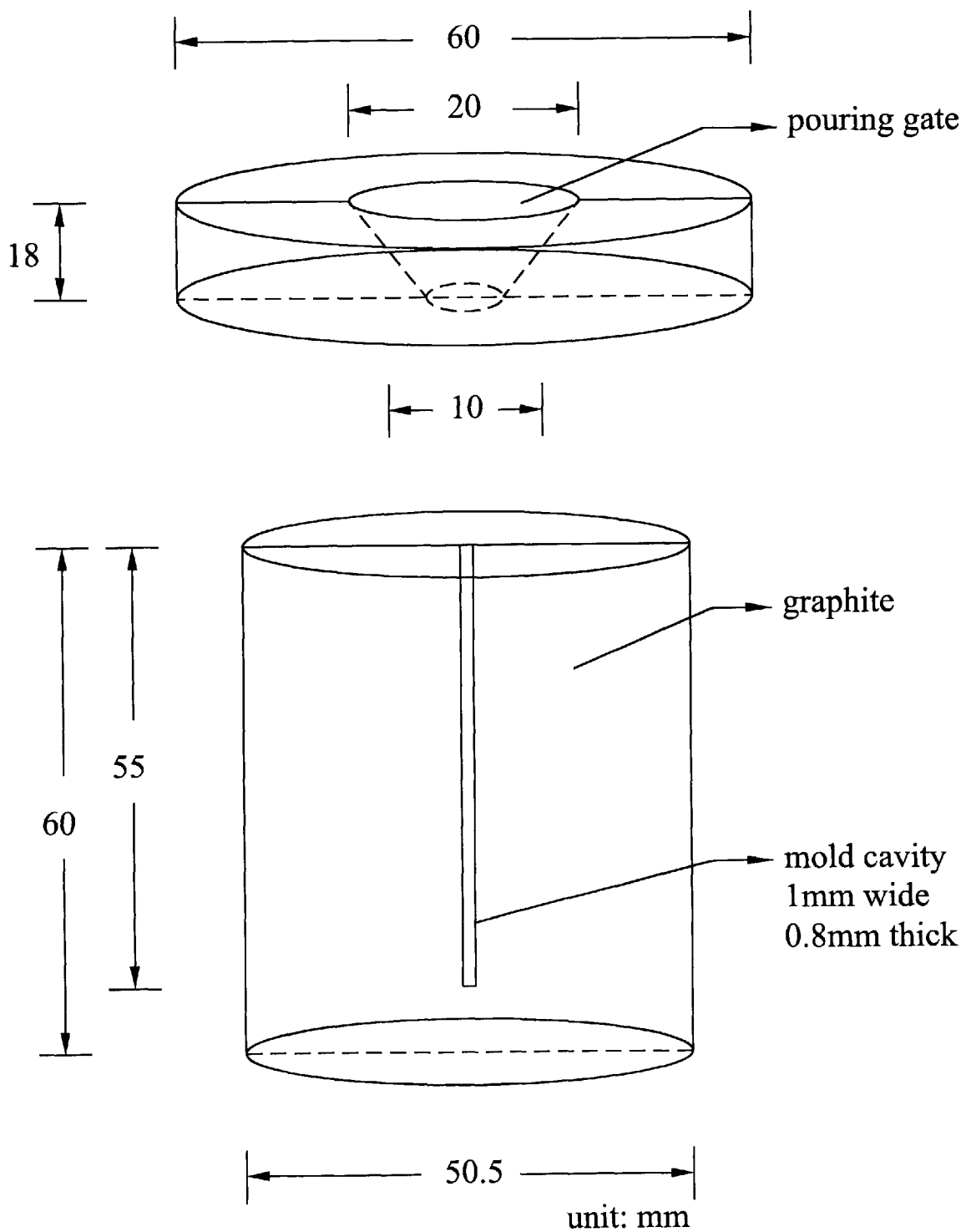
FIG. 3 is a schematic drawing showing the graphite mold used for the castability test in this invention.

FIG. 3 is a schematic drawing showing the graphite mold used in this example. The graphite mold cavity was a uniform 55×1×0.8 mm$^3$ cavity. The casting conditions were the same as mentioned above.

Figure 4:
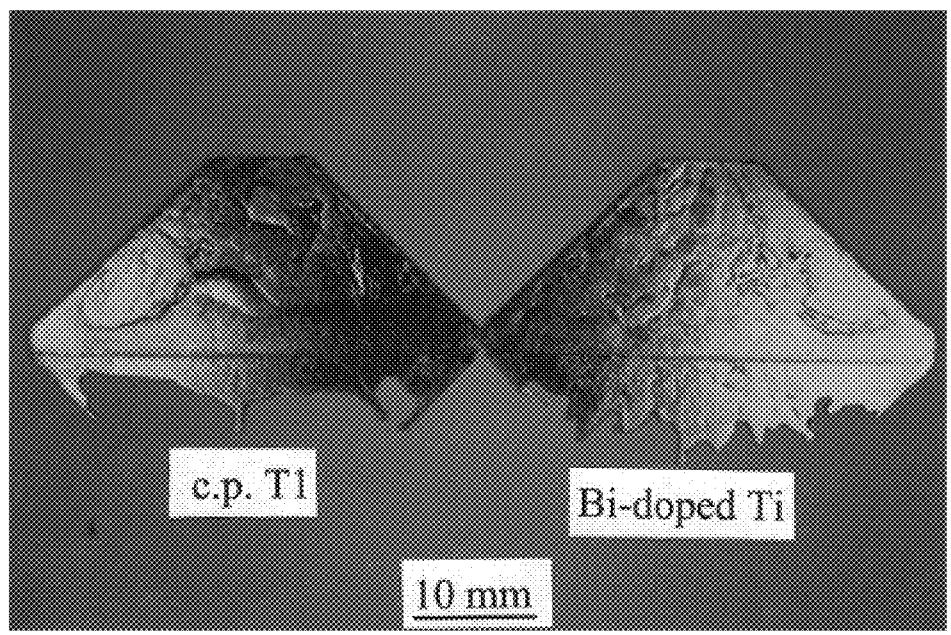
FIG. 4 shows the castings of (a) pure titanium and (b) the titanium containing 1 wt % of Bi obtained from the example, which were both cast in the copper mold.
Figure 5:
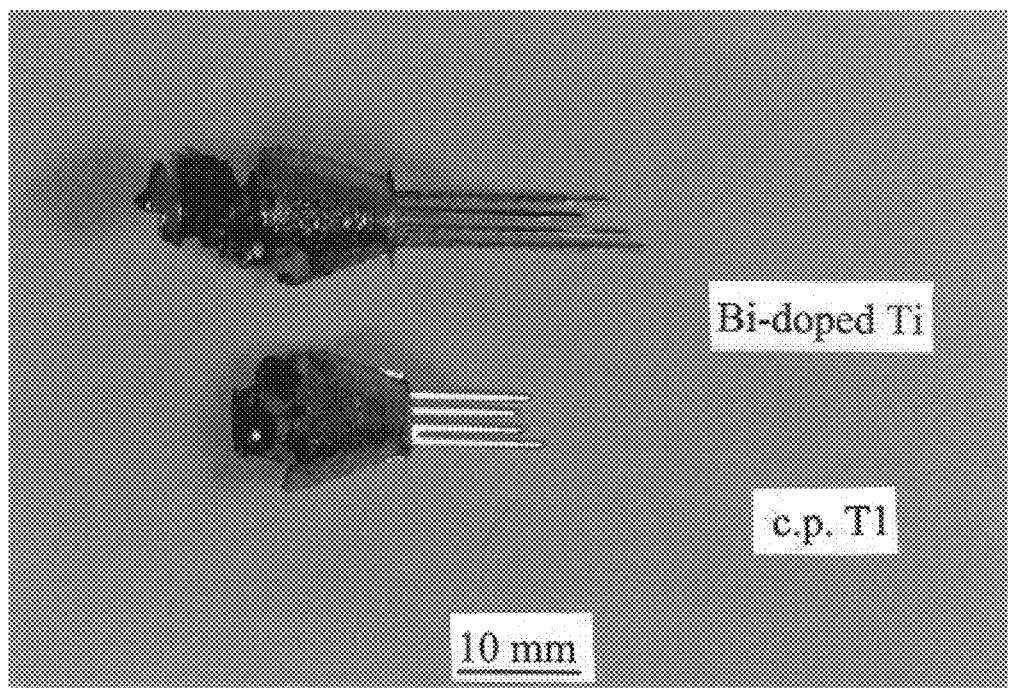
FIG. 5 shows the castings of (a) pure titanium and (b) the titanium containing 1 wt % of Bi obtained from the example, which were both cast in the graphite mold.

FIG. 4 shows the castings of (a) pure titanium and (b) titanium containing 1 wt % of Bi, which are cast in the copper mold. It can be seen that the area of the thinner bottom half of the Bi-doped Ti alloy is larger than that of pure Ti, indicating that the titanium containing 1 wt % of Bi has a better castability than pure Ti. FIG. 5 shows the castings of (a) pure titanium and (b) the titanium containing 1 wt % of Bi, which are cast in the graphite mold. From FIGS. 4 and 5, it can be seen that the bismuth-doped titanium exhibits a higher castability than pure Ti, no matter a copper mold or graphite mold is used for casting.

Figure 6:
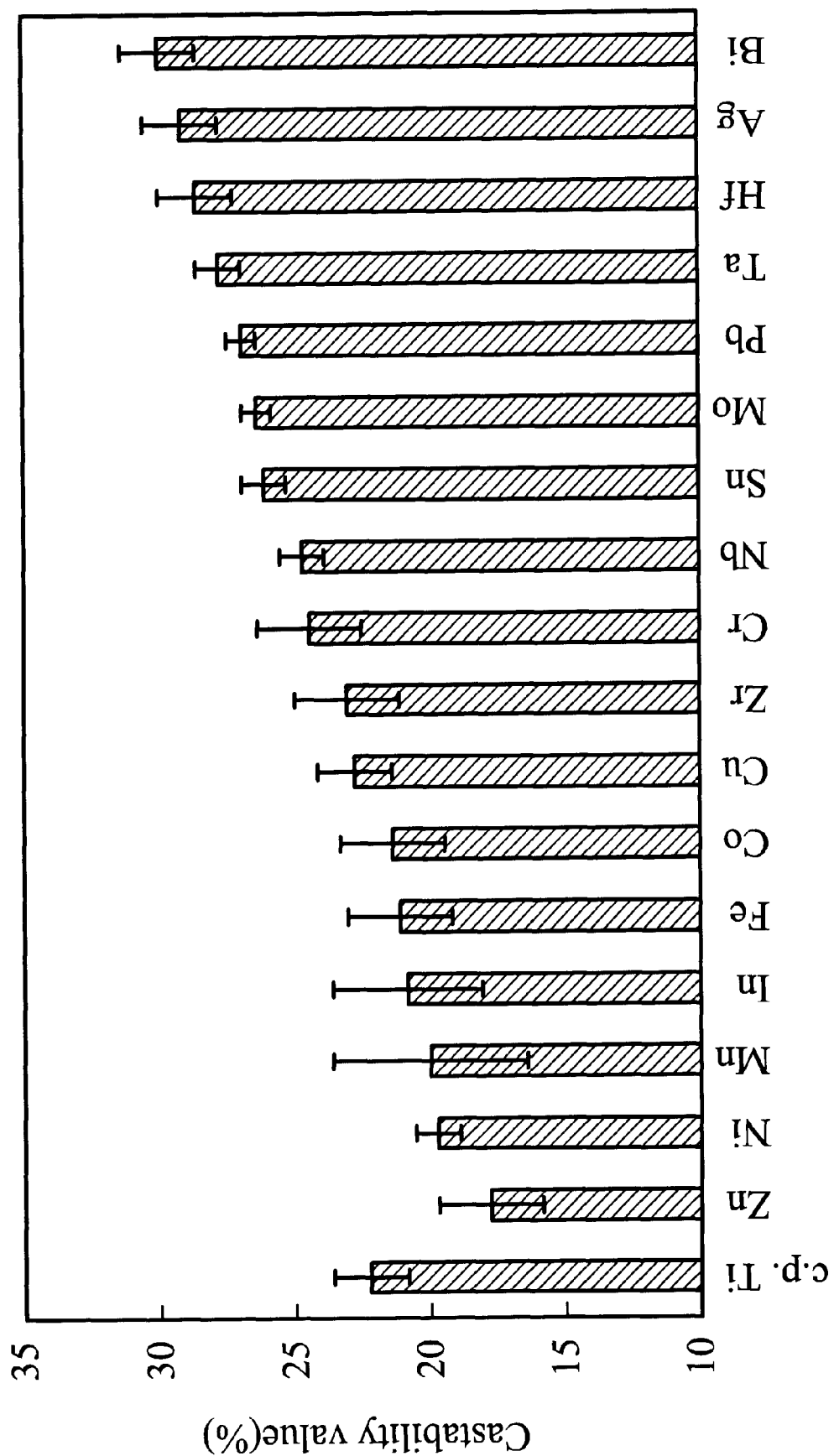
FIG. 6 shows the castability of the titanium according to the present invention in terms of the area percentage of the molten metal filled in the bottom half of the copper mold.

FIG. 6 shows the castability of the nine kinds of titanium in terms of the cast area of the molten metal in the copper mold. The castability values for the metals cast into the copper mold were defined by the ratios of the cast areas in the bottom half cavity to the total bottom half area of the cavity. Each castability value is the average of five repeated tests. It can be seen that the addition of the nine kinds of alloying metals can improve the castability to some extent. The addition of 1 wt % of bismuth and 1 wt % of silver had the best results, making the castability become 29.9% and 29.2% respectively, an increase of 34.4% and 31.4% respectively compared with that of pure titanium (22.2%). The addition of 1 wt % of hafnium, tantalum, molybdenum, tin, niobium, or chromium can improve the castability by 13% to 30% compared with that of pure titanium. As to copper, the castability is improved by only 5%.

Figure 7:
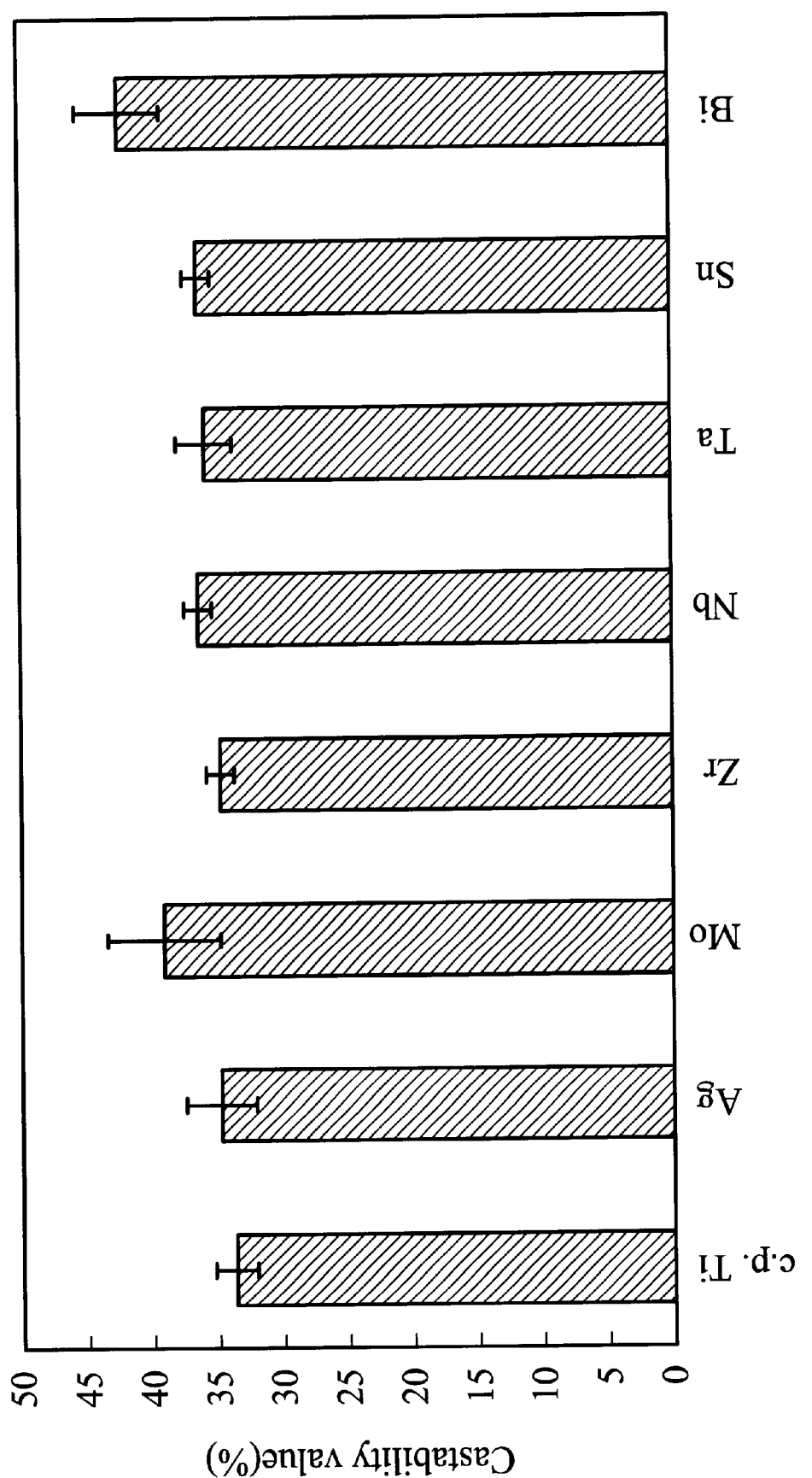
FIG. 7 shows the castability of the titanium according to the present invention in terms of the flowability of the molten metal in the graphite mold.

FIG. 7 shows the castability of the nine kinds of titanium in terms of the ratio of cast length of the molten metal in the graphite mold. The addition of 1 wt % of bismuth and 1 wt % of molybdenum have the best results, making the casting length become 23.3 mm and 21.7 mm respectively, an increase of 24.1% and 15.2% respectively compared with that of pure titanium (18.8 mm). The addition of 1 wt % of tin, tantalum, or niobium can improve the castability by 8.0% to 5.7% compared with that of pure titanium. As to silver, the castability is improved by 2.3% and 3.2% respectively.

Phase and morphology

Figure 8:
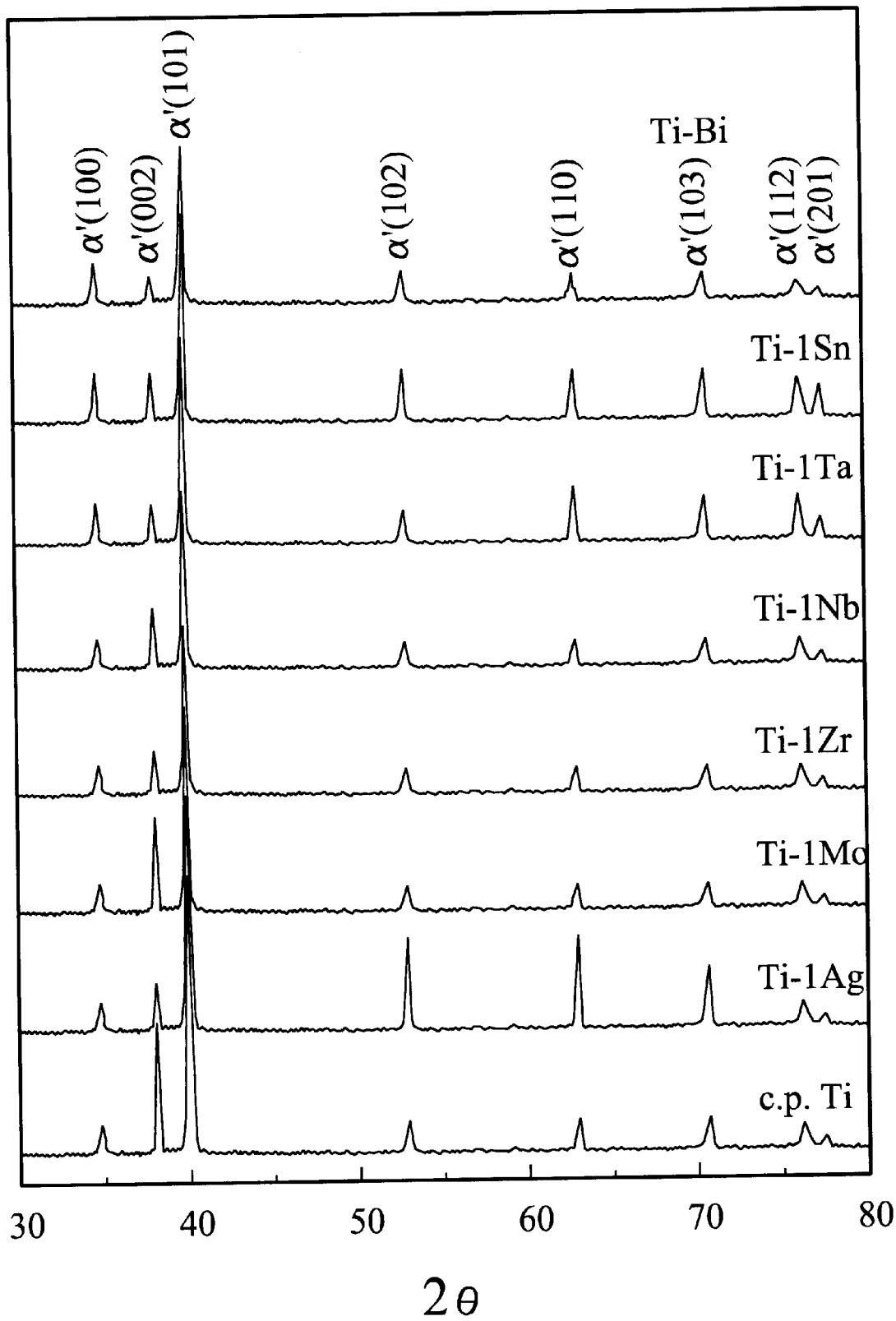
FIG. 8 shows XRD patterns of c.p. Ti and doped Ti.

The XRD results indicated that all doped titanium systems had the same crystal structure (hcp) as that of c.p. Ti due to their minor quantities of alloying additions. The only exception was found in the iron-doped titanium system, in which a slight amount of β phase was retained. This suggests that iron is a very strong β-stabilizer, in agreement with other reports. To save space, the XRD patterns of only seven doped systems on which bending tests were performed are presented (FIG. 8).

Figure 9A:
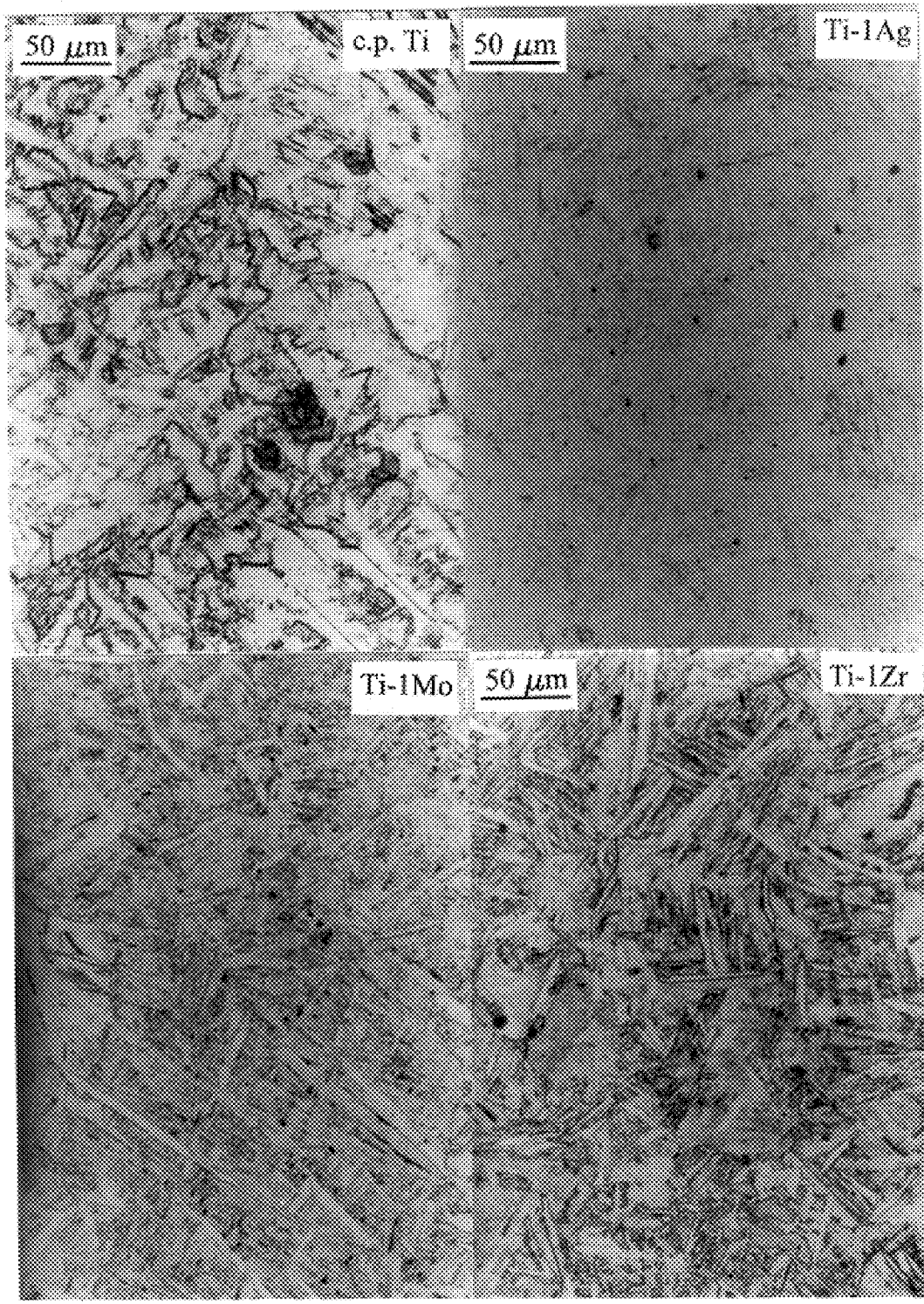
FIGS. 9a and 9b show light micrographs of cast c.p. Ti and doped Ti.
Figure 9B:
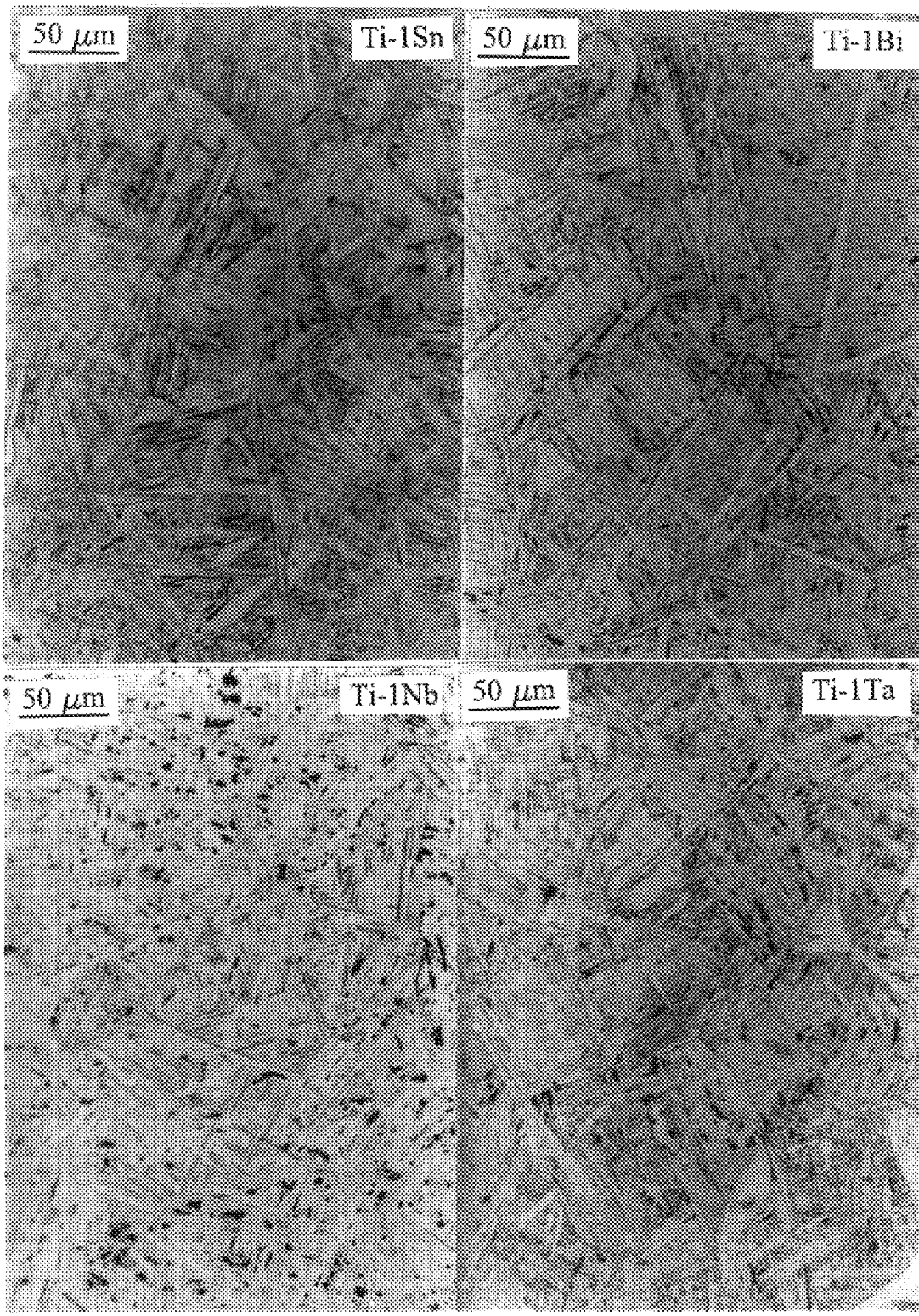

Optical morphology of cast c.p. Ti as well as the same seven doped titanium systems are shown in FIG. 9. Although c.p. Ti and all doped titanium had the same crystal structure, as mentioned earlier, the morphology of doped titanium was quite different from that of c.p. Ti. From optical microscopy point of view, all doped titanium systems had a similar, fine acicular martensitic type structure. The cast c.p. Ti, however, had a much coarser, lath type morphology. This significant difference in morphology is accountable for the significant difference in strength between c.p. Ti and doped titanium, as will be shown later.

Microhardness

Figure 10:
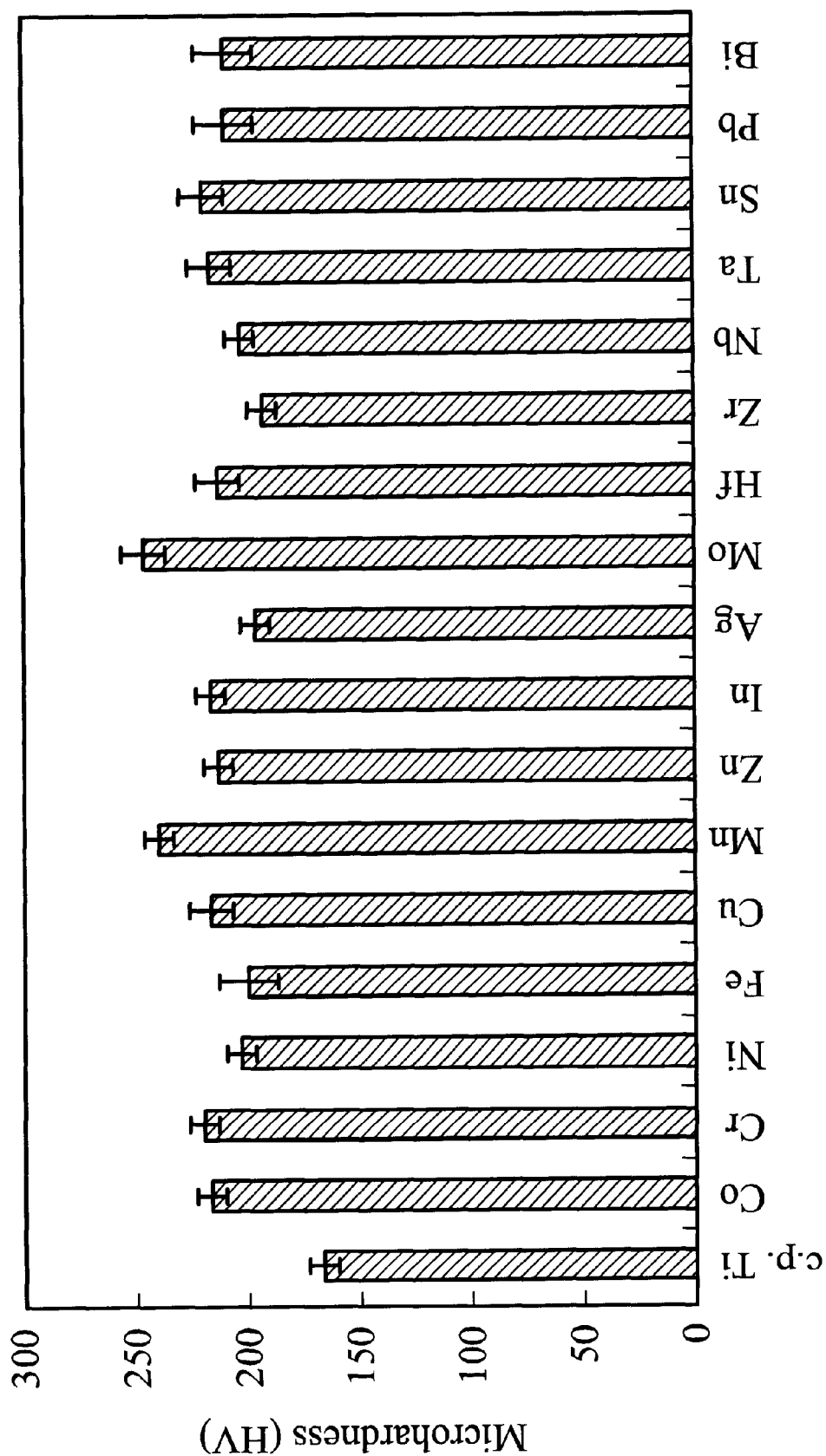
FIG. 10 shows microhardness of cast c.p. Ti and doped Ti.

As shown in FIG. 10, addition of any alloying element used in this study significantly increased the microhardness of titanium. The highest microhardness values were found in the titanium doped with molybdenum, 242 HV (higher than c.p. Ti by 47%), and with manganese, 237 HV (higher than c.p. Ti by 44%). All other doped titanium had microhardness values in the range of 190–220 HV. Since all doped titanium had essentially the same crystal structure and very similar microstructure, as shown earlier, the different microhardness levels should be primarily due to the different solution-hardening effects of the various alloying elements.

Bending strength and modulus

Figure 11:
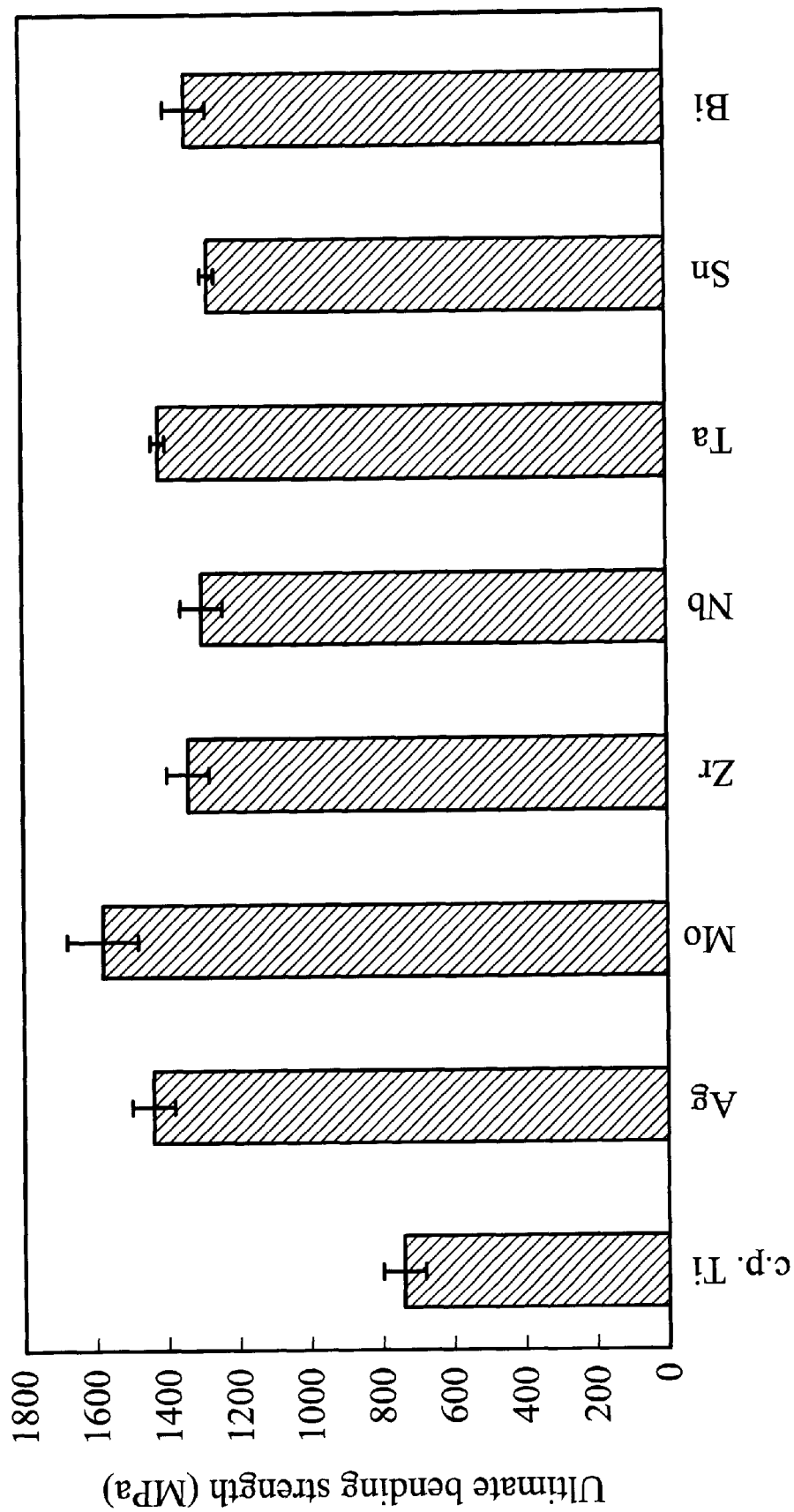
FIG. 11 shows bending strengths of cast c.p. Ti and doped Ti.

Like microhardness, when a minor amount of alloying element was doped, the bending strength of titanium could be significantly increased, as shown in FIG. 11. As a comparison, the bending strength of c. p. Ti was roughly 760 MPa, while all the seven doped titanium systems had bending strengths higher than 1290 MPa. These large increases in strength were attributed to the marked difference in morphology between c.p. Ti and doped titanium, as well as a solution-strengthening effect of alloying addition. The largest bending strength was found in molybdenum-doped titanium (1574 MPa), that was roughly double the bending strength of c.p. Ti. Again, since all the seven doped titanium systems had the same crystal structure and similar morphology, the differences in bending strength among the various doped titanium systems should primarily come from their different solution-strengthening effects.

Figure 12:
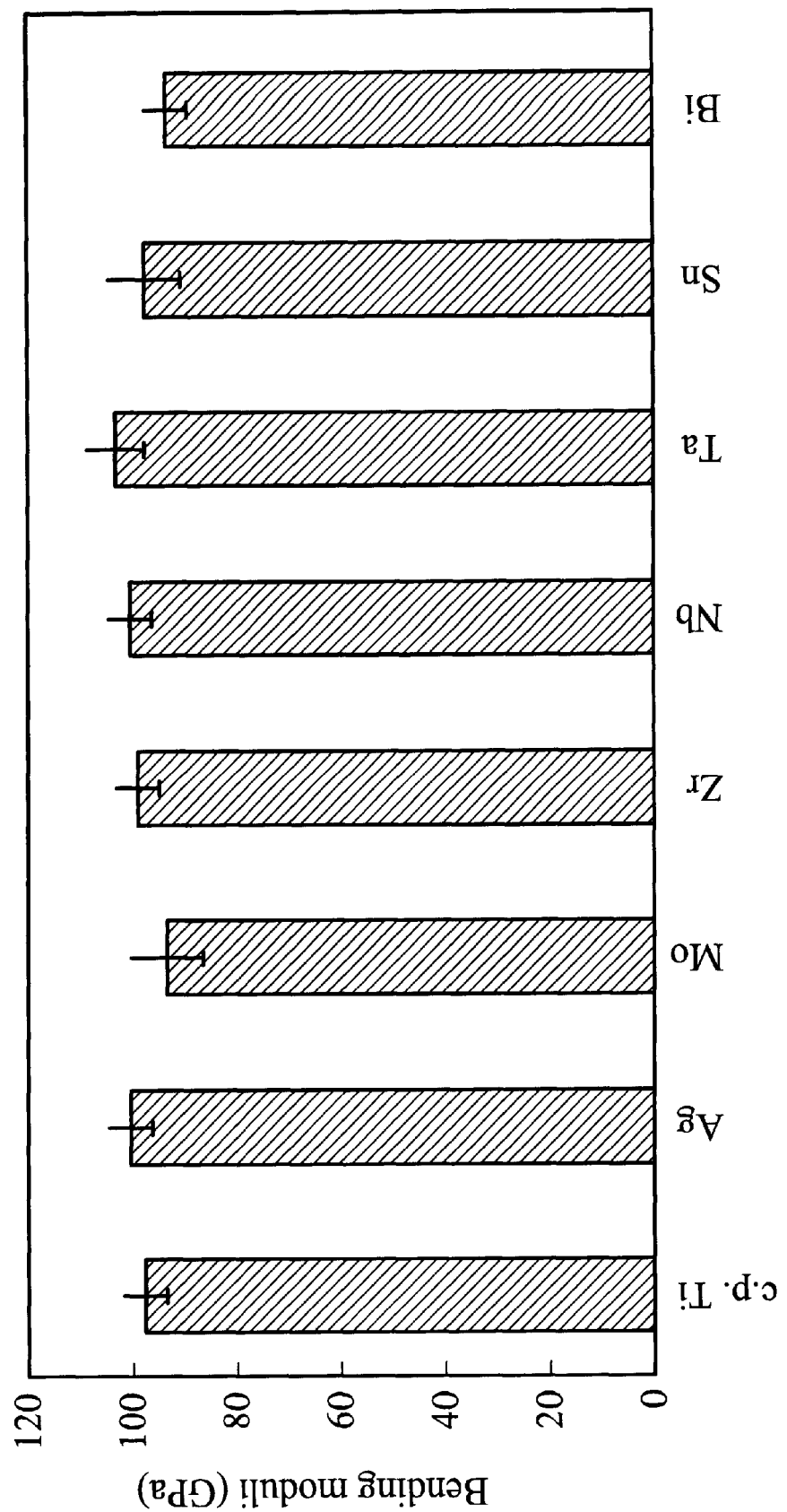
FIG. 12 shows bending moduli of cast c.p. Ti and doped Ti.

Despite their much higher bending strengths, the bending moduli of the seven doped titanium systems (94–104 GPa) were all similar to that of c.p. Ti (98 GPa), as shown in FIG. 12. This was not surprised, since modulus is generally less sensitive to morphology than strength is. The fact that moduli of doped titanium remained the same low level as that of c.p. Ti is important, when an implant application is concerned, where a low modulus material is preferred to avoid the stress-shielding effect.

Although the present invention has been explained by the embodiments shown in the drawings described above, it should be understood to the ordinary skilled person in the art that the invention is not limited to the embodiments, but rather that various changes or modifications thereof are possible without departing from the spirit of the invention. Accordingly, the scope of the invention shall be determined only by the appended claims and their equivalents.

What is claimed is:

1. A biomedical implant formed from a low alloying element doped titanium comprising titanium and from about 0.01 to 3% by weight of an alloying element which is bismuth.

2. A biomedical implant formed from a low alloying element doped titanium comprising titanium and 1% by weight of bismuth based on the weight of the titanium.

3. A biomedical implant formed from a casting cast from a low alloying element doped titanium comprising titanium and from about 0.01 to 3% by weight of an alloying element which is bismuth.

* * * * *